US005859287A

United States Patent [19]

Nicolau et al.

[11] Patent Number: 5,859,287
[45] Date of Patent: Jan. 12, 1999

[54] PROCESS FOR PREPARING VINYL ACETATE UTILIZING A CATALYST COMPRISING PALLADIUM, GOLD, AND ANY OF CERTAIN THIRD METALS

[75] Inventors: Ioan Nicolau; Philip M. Colling, both of Corpus Christi, Tex.

[73] Assignee: Celanese International Corporation, Dallas, Tex.

[21] Appl. No.: 960,888

[22] Filed: Oct. 30, 1997

[51] Int. Cl.$^6$ ............................ C07C 67/00; C07C 67/02
[52] U.S. Cl. ............................ 560/241; 560/261
[58] Field of Search ...................... 560/241, 261

[56] References Cited

U.S. PATENT DOCUMENTS

| | | | |
|---|---|---|---|
| 3,775,342 | 11/1973 | Kronig et al. | 252/430 |
| 3,822,308 | 7/1974 | Kronig et al. | 260/497 |
| 5,314,858 | 5/1994 | Colling | 502/330 |
| 5,332,710 | 7/1994 | Nicolau et al. | 502/243 |
| 5,567,839 | 10/1996 | Gulliver et al. | 560/245 |
| 5,591,688 | 1/1997 | Blum et al. | 502/330 |

FOREIGN PATENT DOCUMENTS

| | | |
|---|---|---|
| 1 246 015 | 9/1971 | United Kingdom . |
| 96/37294 | 11/1996 | WIPO . |

*Primary Examiner*—Gary Geist
*Assistant Examiner*—Rosalynd Keys
*Attorney, Agent, or Firm*—M. Susan Spiering

[57] ABSTRACT

A catalyst for the production of vinyl acetate by reaction of ethylene, oxygen and acetic acid as reactants comprising a porous support on the porous surfaces of which is deposited catalytically effective amounts of metallic palladium and gold and a third metal selected from the group consisting of magnesium calcium, barium, zirconium and cerium, as its oxide or mixture of oxide and metal, said catalyst having been prepared by either of two specified methods (A) or (B). Use of the catalyst results in a reaction of relatively high activity and/or low heavy ends selectivity.

13 Claims, No Drawings

PROCESS FOR PREPARING VINYL ACETATE UTILIZING A CATALYST COMPRISING PALLADIUM, GOLD, AND ANY OF CERTAIN THIRD METALS

BACKGROUND OF THE INVENTION

1. Field of the Invention

This invention relates to new and improved catalysts for the production of vinyl acetate by reaction of ethylene, oxygen and acetic acid.

2. Background Information Including Description of Related Art

It is known to produce vinyl acetate by reaction of ethylene, oxygen and acetic acid using a catalyst consisting of palladium and gold supported on a carrier. While the process utilizing such a catalyst is capable of producing vinyl acetate at relatively high levels of productivity, any expedient resulting in even greater productivity would be very desirable.

The following references may be considered material to the invention claimed herein.

U.S. Pat. Nos. 3,775,342 issued Nov. 27, 1973, and 3,822,308 issued Jul. 2, 1974, both to Kronig et al., each discloses a method of making vinyl acetate catalysts comprising treating a support simultaneously or successively with a solution A containing dissolved salts of noble metals such as palladium and gold and a solution B containing compounds able to react on the support with the noble metal salts to form water insoluble compounds, treating such water-insoluble compounds with a reducing agent to convert the water-insoluble noble metal compounds to the free metals, washing the catalyst to remove water-soluble compounds, and applying an alkali metal compound e.g. an alkali metal carboxylate before or after treatment with the reducing agent. Solution A can optionally also contain salts of other metals such as magnesium, calcium, barium and rare earths.

U.S. Pat. No. 5,332,710, issued Jul. 26, 1994, to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as insoluble compounds on the support by immersing and tumbling the impregnated support in a reactive solution for at least ½ hour to precipitate such compounds, and subsequently reducing the compounds to its metallic form.

U.S. Pat. No. 5,567,839, issued Oct. 22, 1996, to Gulliver et al., discloses a method of producing vinyl acetate catalysts including the step of using a barium "salt", such as barium hydroxide, to precipitate water-insoluble palladium and gold compounds onto a support prior to reduction with a reducing agent. When barium hydroxide is used as precipitant, residual barium remains in the finished catalyst.

SUMMARY OF THE INVENTION

In accordance with this invention, a catalyst is provided useful for the production of vinyl acetate by reaction of ethylene, oxygen and acetic acid, comprising a porous support on the porous surfaces of which is deposited catalytically effective amounts of metallic palladium and gold, and a third metal selected from the group consisting of magnesium, calcium, barium, zirconium and cerium, as its oxide or mixture of oxide and free metal, said catalyst having been prepared by either method (A) comprising the steps of impregnating a porous support with an aqueous solution of water-soluble salts of palladium and said third metal, fixing said palladium and third metal as water-insoluble compounds by reaction with an appropriate alkaline compound, subsequently impregnating the catalyst with a solution of a water-soluble gold salt, fixing the gold in the solution present in the latter impregnation as a water-insoluble compound by reaction with an appropriate alkaline compound, and reducing the fixed palladium and gold to their metallic state and the fixed third metal to its oxide or mixture of oxide and metal; or method (B) comprising the steps of impregnating the support with a solution of water-soluble salts of palladium, gold and said third metal, fixing the palladium, gold, and third metal in the latter solution as water-insoluble compounds by means including the step of rotating and/or tumbling the impregnated support while it is immersed in a solution of an appropriate alkaline compound (roto-immersion), and reducing the fixed palladium and gold to their metallic state and the third metal its oxide or mixture of oxide or metal.

It is believed that vinyl acetate catalysts under the invention containing catalytically effective amounts of palladium, gold and any of the specified third metals prepared by method (A) or (B) perform with more consistently higher activity and/or a lower selectivity to heavy ends, when compared with catalysts not containing such a third metal, than catalysts prepared by various other methods and therefore not under the invention, because the catalysts under the invention have a more consistent and predictable composition with a greater degree of homogeneity than catalysts prepared by other methods. Such higher activity and/or lower heavy ends selectivity often results in greater vinyl acetate productivity than if no third metal is employed.

DETAILED DESCRIPTION OF THE INVENTION

In preparing the catalysts under this invention using method (A) or (B), the catalyst support material is composed of particles having any of various regular or irregular shapes, such as spheres, tablets, cylinders, rings, stars, or other shapes, and may have dimensions such as diameter, length, or width of about 1 to about 10 mm, preferably about 3 to 9 mm. Spheres having a diameter of about 4 to about 8 mm are preferred. The support material may be composed of any suitable porous substance, e.g., silica, alumina, silica-alumina, titania, zirconia, silicates, aluminosilicates, titanates, spinel, silicon carbide, or carbon and the like.

The support material may have a surface area within the range, for example, of about 10 to about 350, preferably about 100 to about 200 $m^2/g$, an average pore size in the range, for example, of about 50 to about 2000 angstroms, and a pore volume in the range, for example, of about 0.1 to 2, preferably about 0.4 to about 1.2 ml/g.

In carrying out the impregnation of the support material with water soluble salts of the contemplated catalytically active metals, palladium (II) chloride, sodium palladium (II) chloride, potassium palladium(II) chloride, palladium (II) nitrate or palladium (II) sulfate are examples of suitable water-soluble palladium compounds, while alkali metal, e.g., sodium or potassium salts of auric (III) chloride or tetrachloroauric (II) acid are examples of water-soluble gold compounds which can be used. Depending on which third metal is desired in the catalyst, the following water-soluble salts are examples of compounds which can be used for the impregnation of such third metal: magnesium sulfate (anhydrous or hydrated), magnesium acetate (anhydrous or hydrated), magnesium chloride (anhydrous or hydrated), or magnesium nitrate (hydrated); calcium chloride (anhydrous or hydrated), calcium acetate (anhydrous or monohydrate), or calcium nitrate (anhydrous or hydrated); barium acetate (anhydrous or hydrated), or barium nitrate (anhydrous); zirconium sulfate tetrahydrate, zirconium chloride, or zirconium nitrate (anhydrous or pentahydrate); or cerous nitrate (hydrated); cerous chloride (anhydrous), cerous sulfate (anhydrous or hydrated), or cerous acetate (anhydrous or hydrated).

In preparing the catalyst by method (A) or (B), the impregnations of the support material with solutions of water-soluble salts of the catalytically active metals may be effected by any method known to those skilled in the art. Preferably, however, such impregnations are accomplished by the "incipient wetness" method wherein an amount of water-soluble salt solution used for the impregnation is from about 95 to about 100 percent of the absorptive capacity of the support material. While the quantities of water-soluble salts of palladium and the third metal equivalent to the entire amounts of these metals in the finished catalyst may be present in the first impregnation carried out in method (A) or (B), it is often advantageous for the quantity of water-soluble gold salt in the first impregnation carried out in method (B), or in the first impregnation containing gold salt after the fixing as described hereinafter of palladium and third metal in method (A), to contain only part of the elemental gold desired in the finished catalyst. In either case, after the fixing as described hereinafter of that part of the gold in the first impregnation with a solution of water-soluble gold salt, a further impregnation is carried out with a solution of gold salt equivalent to the remainder of the gold desired in the finished catalyst. The impregnations are such as to provide, for example, about 1 to about 10 grams of elemental palladium; and for example, about 0.5 to about 10 grams of elemental gold, per liter of finished catalyst, with the amount of gold being from about 10 to about 125 weight percent based on the weight of palladium. Depending on which third metal is desired in the catalyst and assuming such third metal is the only one present, the number of grams of elemental third metal per liter of catalyst provided by the impregnation may be, for example, within the following ranges.

magnesium: about 0.1 to about 2.0, preferably about 0.3 to about 1.0;

calcium: about 0.2 to about 4.0; preferably about 0.5 to about 1.5;

barium: about 0.2 to about 5.0, preferably about 0.6 to about 3.0;

zirconium: about 0.4 about to 7.0, preferably about 1.0 to about 3.0;

cerium: about 0.5 to about 10.0, preferably about 1.8 to about 5.0.

After each impregnation of the support with an aqueous solution of water-soluble salt of a catalytically active metal, the metal is "fixed", i.e., precipitated, as a water-insoluble compound such as the hydroxide, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkaline compound should be in an amount of, for example, about 1 to about 2, preferably about 1.1 to about 1.8 times the amount necessary to completely precipitate the cations of the catalytically active metals present.

In method (A) of catalyst preparation, each fixing of the metal may be done by the incipient wetness method wherein the impregnated support is dried, e.g., at a temperature of about 150° C. for one hour, contacted with an amount of solution of the alkaline material equal to about 95–100% of the pore volume of the support, and allowed to stand for a period of about ½ hour to about 16 hours; or the roto-immersion method wherein the impregnated support without drying is immersed in a solution of the alkaline material and is rotated and/or tumbled during at least the initial period of precipitation such that a thin band of the precipitated water-soluble compound is formed at or near the surface of the support particles. In method (B) the fixing of the metals in the palladium and third metal salts added by the first impregnation must by done by roto-immersion. However, the fixing of the gold in the water-soluble gold salt added in any subsequent impregnation may be accomplished by incipient wetness or roto-immersion. In carrying out the fixing of metals by roto-immersion, the rotation and tumbling may be carried out, for example, at about 1 to about 10 rpm for a period of, for example, at least about 0.5 hour, preferably about 0.5 to about 4 hours. The contemplated roto-immersion method is disclosed in previously cited U.S. Pat. No. 5,332,710, the entire disclosure of which is incorporated herein by reference.

The fixed, i.e., precipitated palladium, gold and third metal compounds may be reduced, for example, in the vapor phase with ethylene, e.g., 5% in nitrogen at 150° C. for 5 hours after first washing the catalyst containing the fixed metal compounds, until it is free of anions such as halide, and drying, e.g., at 150° C. for about 1 hour, or such reduction may be accomplished before washing and drying in the liquid phase at room temperature with an aqueous solution of hydrazine hydrate wherein the excess of hydrazine over that required to reduce all the metal compounds present on the support is in the range, for example, of about 8:1 to about 15:1, followed by washing and drying. Other reducing agents and means for reducing the fixed metal compounds present on the support may be employed as conventional in the art. The reduction of the fixed palladium and gold compounds mainly results in the formation of the free metal, although a minor amount of metal oxide may also be present, while the reduction of the fixed third metal generally results in the formation of an oxide or a mixture of oxide and free metal, depending on reduction conditions and which third metal is present. In preparations using more than one impregnation and fixing steps, the reduction may be carried out after each fixing step or after the total of the metallic elements have been fixed on the support.

In a preferred embodiment of method (A), using the specific procedures described previously, the support is first impregnated with an aqueous solution of water-soluble compounds of palladium and third metal by incipient wetness, and the palladium and third metal are then fixed by treatment with an alkaline fixing solution by incipient wetness or roto-immersion, preferably roto-immersion. The catalyst is then dried and separately impregnated with a solution of a soluble gold compound having the amount of elemental gold desired in the catalyst, and the gold is fixed by treatment with an alkaline fixing solution by incipient wetness or roto-immersion, preferably incipient wetness. If the gold is to be fixed by the incipient wetness method, such fixing may be combined with the impregnation step by using a single aqueous solution of soluble gold compound and alkaline fixing compound in an amount in excess of that necessary to convert all the gold in the solution to a fixed insoluble gold compound, e.g., auric hydroxide. If a hydrocarbon such as ethylene, or hydrogen is to be used in the vapor phase as reducing agent, the catalyst containing the fixed metal compounds is washed until it is free of dissolved anions, dried, and reduced with ethylene or other hydrocarbon as previously described. If hydrazine is to be used in the liquid phase as reducing agent, the catalyst containing the fixed metal compounds is treated with an aqueous solution of excess hydrazine hydrate before washing and drying to reduce the metal compounds to the free metals, and the catalyst is then washed and dried as described.

In a preferred embodiment of method (B), in which only part of the gold is impregnated with the palladium and the third metal in a first impregnation, the metals are fixed by reaction with an alkaline fixing compound by roto-immersion, the fixed metal compounds are reduced to the free metals, e.g., with ethylene or hydrazine hydrate, with washing and drying done before an ethylene reduction or after a hydrazine reduction. The catalyst is then impregnated with the remainder of the gold which is fixed on the catalyst using any of the procedures described previously. Preferably the impregnation and fixing are accomplished in a single step by incipient wetness using a single solution of a water-soluble gold compound and an appropriate alkaline compound. The added, fixed gold is then reduced, e.g., with ethylene or hydrazine, after or before washing and drying, as described previously.

After the catalyst containing palladium and gold in metallic form and third metal as oxide or mixture of oxide and metal deposited on a support material is prepared by any of the foregoing methods, it is advantageously further impregnated with a solution of an alkali metal acetate, preferably potassium or sodium acetate, and most preferably potassium acetate. The catalyst is then dried such that the finished catalyst contains, for example, about 10 to about 70, preferably about 20 to about 60 grams of alkali metal acetate per liter of finished catalyst.

While the catalysts of this invention have been described a containing only one "third" metal, more than one of such metals can actually be present. When at least two of such described "third" metals are desired in the catalyst, the initial impregnating solution will contain dissolved salts of these metals to provide such metals in the finished catalyst within ranges, the upper and lower limits of each of which is a fraction of the limits defined previously on the assumption that only a single "third" metal is present, such fraction being the same as the fraction that the individual "third" metal is of the total amount of third metal in the catalyst.

When vinyl acetate is prepared using a catalyst according to the present invention, a stream of gas, which contains ethylene, oxygen or air, acetic acid, and desirably an alkali metal acetate, is passed over the catalyst. The composition of the gas stream can be varied within wide limits, taking into account explosive limits. For example, the molar ratio of ethylene to oxygen can be about 80:20 to about 98:2, the molar ratio of acetic acid to ethylene can be about 100:1 to about 1:100, preferably about 10:1 to about 1:8, and the content of gaseous alkali metal acetate can be about 1 to about 100 ppm based on the weight of acetic acid employed. The alkali metal acetate may be conveniently added to the feed stream as a spray of an aqueous solution of such acetate. The gas stream also can contain other inert gases, such as nitrogen, carbon dioxide and/or saturated hydrocarbons. Reaction temperatures which can be used are elevated temperatures, preferably those in the range of about 150°–220° C. The pressure employed can be a somewhat reduced pressure, normal pressure or elevated pressure, preferably a pressure of up to about 20 atmospheres gauge.

The following non-limiting examples further illustrate the invention.

COMPARATIVE EXAMPLE A AND EXAMPLES 1 TO 5

These examples illustrate the preparation of catalysts under the invention by method (A) and the advantages of such catalysts in the production of vinyl acetate in terms of higher activity and/or lower heavy ends selectivity.

In Comparative Example A which served as a control, a support material consisting of Sud Chemie KA-160 silica spheres having a nominal diameter of 5 mm, a surface area of about 160 to 175 $m^2/g$, and a pore volume of about 0.68 ml/g, was first impregnated by incipient wetness with an aqueous solution of sodium palladium (II) chloride sufficient to provide about 7 grams of elemental palladium per liter of catalyst. The palladium was then fixed to the support as palladium (II) hydroxide by treating the catalyst by roto-immersion with an aqueous sodium hydroxide solution such that the Na/Cl molar ratio was about 1.2:1. The catalyst was then dried at 100° C. for 1 hour in a fluid bed drier following which it was impregnated by incipient wetness with an aqueous solution of sodium tetrachloroaurate in an amount sufficient to provide the catalyst with 4 grams/liter of elemental gold, and sodium hydroxide such that the Na/Cl mole ratio was about 1.8:1, to fix the gold on the support as auric hydroxide. The catalyst was then water washed until chloride free (about 5 hours) and dried at 150° C. for one hour in nitrogen flow. The palladium and auric hydroxides were then reduced to the free metals by contacting the catalyst with ethylene (5% in nitrogen) in the vapor phase at 150° C. for 5 hours. Finally the catalyst was impregnated by incipient wetness with an aqueous solution of potassium acetate in an amount sufficient to provide 40 grams of potassium acetate per liter of catalyst, and dried in a fluid bed drier at 100°–150° C. for one hour.

In Examples 1 to 5, the procedure of Comparative Example A was followed except that the solution of sodium palladium (II) chloride contained in addition varying amounts of a dissolved salt of a third metal which was subsequently fixed on the support as the hydroxide together with the palladium (II) hydroxide and reduced with ethylene to the oxide or mixture of oxide and metal together with the metallic palladium and gold. The third metal salts were, respectively, magnesium sulfate (Example 1), calcium chloride (Example 2), barium chloride (Example 3), zirconium sulfate (Example 4), and cerous nitrate (Example 5).

The catalysts prepared as described in Examples 1–5 were tested for their activity in the production of vinyl acetate by reaction of ethylene, oxygen and acetic acid. To accomplish this, about 60 ml of each type of catalyst prepared in the examples were placed in separate stainless steel wire baskets. The temperature of each basket was measured by a thermocouple at both the top and bottom of each basket. Each reaction basket was placed in a Berty continuously stirred tank reactor of the recirculating type and was maintained at a temperature which provided about 45% oxygen conversion with an electric heating mantle. A gas mixture of about 130 l/hr (measured at N.T.P.) of ethylene, about 26 l/hr of oxygen, about 128 l/hr of nitrogen, about 131 g/hr of acetic acid, and about 2 mg/hr of potassium acetate, was caused to travel under pressure at about 12 atmospheres through each basket. The reaction was terminated after about 18 hours. Analysis of the products was accomplished by on-line gas chromatographic analysis combined with off-line liquid product analysis by condensing the product stream at about 10° C. to obtain optimum analysis of the end products.

Table I shows for each example the identity and amount in grams per liter of catalyst of the elemental third metal in the catalyst (3rd Met., g/L) in addition to the 7 g/L of palladium and 4 g/L of gold, and the results of the analysis of the reaction product in terms of percent selectivity of $CO_2$ ($CO_2$,% Sel.) and heavy ends, (HE, % Sel.) and relative activity of the reaction expressed as an activity factor (Act.) which is computer calculated in the following way: The computer program uses a series of equations that correlates the activity factor with the catalyst temperature (during the reaction), oxygen conversion, and a series of kinetic parameters for the reactions that take place during vinyl acetate synthesis. More generally, the activity factor is inversely related to the temperature required to achieve constant oxygen conversion.

TABLE I

| Example | 3rd Met, g/L | $CO_2$, % Sel. | HE, % Sel. | Act. |
|---|---|---|---|---|
| A | — | 8.87 | 1.47 | 2.34 |
| 1 | Mg, 0.53 | 9.35 | 1.39 | 2.45 |
| 2 | Ca, 0.88 | 9.28 | 1.88 | 2.50 |
| 3 | Ba, 1.07 | 9.92 | 1.32 | 2.4 |
| 4 | Zr, 2.0 | 8.89 | 1.45 | 2.61 |
| 5 | Ce, 3.1 | 9.35 | 1.13 | 2.45 |

As shown in Table I, the catalysts of Examples 1 to 5 each prepared by method (A) and containing one of the specified third metals in addition to constant amounts of palladium and gold, resulted in reactions having a higher activity factor than the catalyst of Comparative Example A containing the same amounts of palladium and gold but no third metal. Furthermore the catalysts of Examples 1, 3 and 5 containing magnesium, barium, and cerium respectively as a third metal, also resulted in a reaction having a significantly lower heavy ends selectivity than the reaction of Comparative Example A wherein the catalyst had no third metal.

EXAMPLES 6, 7 AND 8

These examples illustrate the preparation of catalysts under the invention by method (B) and the results of the use of such catalysts in vinyl acetate production, in the same terms as those shown for the catalysts of Examples 1–5.

The same support as used in Comparative Example A and Examples 1–5 was first impregnated by the incipient wetness method with a solution of palladium, gold and third metal salts sufficient to provide 7 grams of elemental palladium, 4 grams of elemental gold, and varying amounts of the elemental third metal. The palladium and gold salts used were the same as in the previous examples, and the third metal salts were magnesium sulfate in Example 6, calcium chloride in Example 7 and barium chloride in Example 8. The metals were then fixed by roto-immersion in an aqueous solution of about 120% of the amount of sodium hydroxide necessary to precipitate the palladium, gold, and third metal, and the latter metals were reduced in the liquid phase using an aqueous solution of hydrazine hydrate at an excess weight ratio of hydrazine to metals of 12:1. After the reduction the catalyst was washed until chloride free (about 5 hours), dried at 100° C. for 1 hour in a fluid drier, and then impregnated by incipient wetness with an aqueous solution of gold salt sufficient to provide the catalyst with 3 additional grams per liter of elemental gold (for a total of 7), and sodium hydroxide such that the Na/Cl mole ratio was about 1.8:1, to fix the additional gold. The additional gold was then reduced in the liquid phase with hydrazine hydrate as described previously, and the catalyst was washed, dried, and impregnated with potassium acetate as described in Comparative Example A. The catalysts were then tested for their function in the production of vinyl acetate as described in the previous example.

Table II gives the identity and amount of third metal in the catalyst in addition to the 7 g/L each of palladium and gold, and also the results of the reaction in terms of percent selectivity of ethylene to $CO_2$ and heavy ends, and the activity factor.

TABLE II

| Example | 3rd Met, g/L | $CO_2$, % Sel. | HE, % Sel. | Act. |
|---|---|---|---|---|
| 6 | Mg, 0.53 | 9.98 | 1.33 | 2.10 |
| 7 | Ca, 0.88 | 10.20 | 1.40 | 2.44 |
| 8 | Ba, 3 | 9.91 | 1.34 | 2.44 |
| *9 | — | 9.90 | 1.58 | 2.34 |

*reduced with ethylene; the 3rd metal catalysts 6 through 8 are reduced with hydrazine.

The results of Table II indicate that the third metal containing catalysts of Examples 6, 7, and 8 functioned in the production of vinyl acetate from ethylene, acetic acid, and oxygen with relatively high activity factors and/or low heavy ends selectivities.

I claim:

1. A process for the production of vinyl acetate by reaction of ethylene, oxygen and acetic acid as reactants comprising contacting said reactants with a catalyst comprising a porous support on the porous surfaces of which is deposited catalytically effective amounts of metallic palladium and gold and a third metal selected from the group consisting of magnesium, calcium, barium, zirconium and cerium, as its oxide or mixture of oxide and metal, said catalyst having been prepared by either method (A) comprising impregnating a porous support with an aqueous solution of water-soluble salts of palladium and said third metal, fixing said palladium and third metal as water-insoluble compounds by reaction with an appropriate alkaline compound, subsequently impregnating the catalyst with a solution of a water-soluble gold salt, fixing the gold in the solution present in the latter impregnation as a water-insoluble compound by reaction with an appropriate alkaline compound, and reducing the fixed palladium and gold to their metallic state and the third metal as its oxide or mixture of oxide and metal; or method (B) comprising the steps of impregnating the support with a solution of water-soluble salts of palladium, gold and said third metal, fixing the palladium, gold, and third metal in the latter solution as water-insoluble compounds by means including the step of rotating and/or tumbling the impregnated support while it is immersed in a solution of an appropriate alkaline compound, and reducing the fixed palladium and gold to their metallic state and the third metal to its oxide or mixture of oxide and its metal.

2. The process of claim 1 wherein said third metal is magnesium.

3. The process of claim 1 wherein said third metal is calcium.

4. The process of claim 1 wherein said third metal is barium.

5. The process of claim 1 wherein said third metal is zirconium.

6. The process of claim 1 wherein said third metal is cerium.

7. The process of claim 1 wherein said catalyst has been prepared by method (A).

8. The process of claim 1 wherein said catalyst has been prepared by method (B).

9. The process of claim 8 wherein said step in method (B) of rotating and/or tumbling the impregnated support immersed in a solution of an appropriate alkaline compound to fix the palladium, gold, and third metal, is continued for at least about 0.5 hour.

10. The process of claim 8 wherein said method (B) has been carried out such that said impregnating solution contains all of the elemental palladium and third metal but only part of the elemental gold desired in the finished catalyst; after said fixing and reduction of said catalytically active metals in said impregnating solution, the catalyst is impregnated with another solution containing dissolved therein the remaining elemental gold desired in the catalyst in the form of a dissolved gold salt and an amount of an appropriate alkaline compound sufficient to fix the added gold as a water-insoluble compound; and said fixed added gold is reduced to its metallic state.

11. The process of claim 1 wherein said catalyst contains an alkali metal acetate deposited on the catalyst after the reduction of all the palladium, gold and third metal in the catalyst.

12. The process of claim 11 wherein said alkali metal acetate is potassium acetate.

13. The process of claim 12 wherein potassium acetate is fed to the reaction together with said reactants.

* * * * *